United States Patent [19]

Cole

[11] Patent Number: 4,607,915

[45] Date of Patent: Aug. 26, 1986

[54] LIGHT ABSORBERS

[76] Inventor: Martin T. Cole, 29 Stafford St., Huntingdale, Victoria, Australia

[21] Appl. No.: 640,351

[22] Filed: Aug. 13, 1984

[30] Foreign Application Priority Data

Aug. 12, 1983 [AU] Australia .................. PG0821

[51] Int. Cl.⁴ ............................................. G02B 00/00
[52] U.S. Cl. .............................. 350/321; 350/276 SL
[58] Field of Search ............................ 250/574, 575; 350/276 SL, 319, 321; 356/337, 338, 339, 340, 343

[56] References Cited

U.S. PATENT DOCUMENTS

| 3,185,975 | 5/1965 | Kompelien | 250/574 |
| 4,166,960 | 9/1979 | Meili | 250/575 |
| 4,315,158 | 2/1982 | Kakigi et al. | 250/574 |

Primary Examiner—John K. Corbin
Assistant Examiner—Vincent J. Lemmo
Attorney, Agent, or Firm—Learman & McCulloch

[57] ABSTRACT

A light absorber for use in a sampling tube used with sensitive optical pollution detectors the light absorber including a central light receiving conical surface inclined by at least one annular truncated conical surface to provide at least one annular groove or valley surrounding the central cone and wherein one wall of the groove or valley is undercut to shade the base of the groove or valley from direct impinging light.

11 Claims, 2 Drawing Figures

U.S. Patent  Aug. 26, 1986  4,607,915
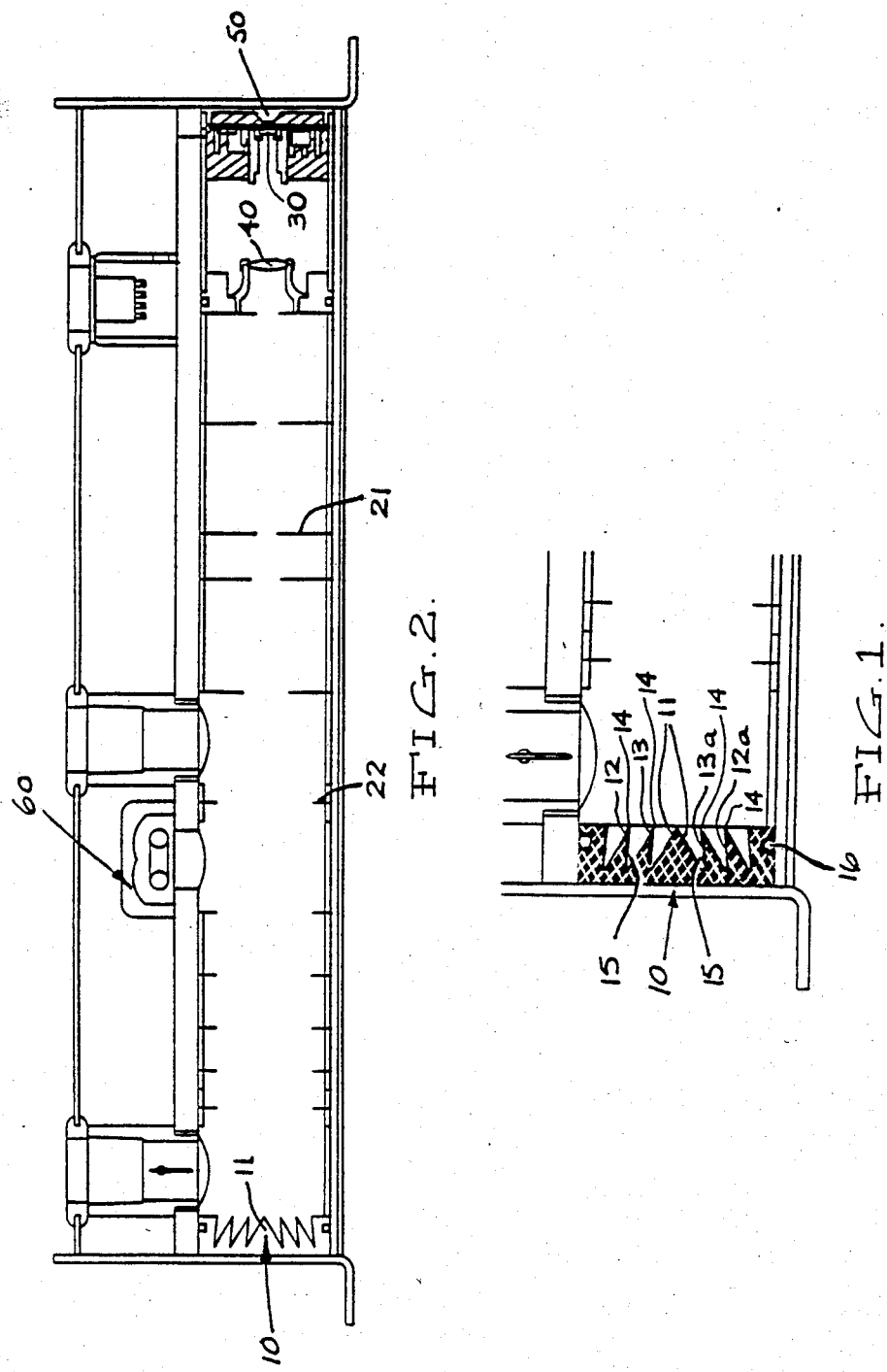

LIGHT ABSORBERS

The present invention relates to a light absorber device which is effective to prevent or restrict reflection of light perpendicular to its surface over a wide range of incident angles.

The light absorber of the present invention has particular though not exclusive application in extremely sensitive optical smoke detectors incorporating at least one tubular sampling chamber including a light sensing device at one end, a light absorber at the other end, a light source projected across the tube, means for taking continuous samples of surrounding air whereby when smoke is present light impinges on the sensing device thereby creating an alarm situation. Thuss, by detecting the presence of smoke it may be possible to indicate the presence of fire at a very early stage so that action can be taken prior to major damage being caused. Unfortunately, sufficiently sensitive known apparatus is subject to spurious response because of lack of, or poorly controlled sensitivity. Furthermore, such known smoke detection apparatus are rather large and heavy, and require relatively high powers to operate them.

One important aspect of smoke detector construction is to provide an air sampling tube of short length.

One factor which contributes to the overall dimension of the chamber is the provision of an effective light absorber. The absorber is designed to prevent light from being reflected perpendicular to the surface of the absorber. Thus, when installed into a sampling chamber the absorber prevents light directed towards the absorber from any angle being reflected back along the sampling chamber towards the light sensing device. Thus no light should be reflected axially along the sampling chamber.

Devices are known utilising a blackened inclined plane to reflect light towards the blackened walls of said sampling chamber, thereby to absorb light by at least three lossy reflections before the remnant light can be returned in the direction of said detector element.

Another known absorber utilises a blackened cone, concentric with said sampling chamber. This has the advantage of halving the length which would have been occupied by said inclined plane, assuming the half-apex angle of said cone equals the angle of inclination of said plane to said sampling chamber. The external length of said sampling chamber is thereby reduced.

The present invention has as a principal objective the provision of a light absorber which is effective yet simple to construct.

There is provided according to the present invention a light absorber including a substantially central light receiving conical surface surrounded by at least one annular conical surface to provide at least one annular groove or valley surrounding said central conical surface.

There is provided according to a specific aspect of the present invention a light absorber including a central light receiving conical surface surrounded by at least one annular groove or valley surrounding said central cone wherein one wall of the groove or valley is undercut to shade the base of the groove or valley from direct impinging light.

Conveniently, there are a plurality of undercut valleys in a cylindrical body constituting the absorber device. The surface of the device is coated with a material which is highly light absorptive. The absorber of the present invention will absorb light with greater efficiency while occupying a length at least 3 times shorter than a simple cone absorber and at least 6 times shorter than an inclined plane absorber as mentioned above.

Thus, the present invention when applied to an optical smoke sampling chamber is not only effective in minimising the external length of the chamber but is more effective. Thus, the number of applications in which the smoke detector fitted with the absorber can be used is increased because of its compactness. The invention will be described with reference to the accompanying drawings in which:

FIG. 1 shows a cross sectional view of an absorber mounted at one end of a sampling tube, only part of which is shown; and FIG. 2 shows a cross sectional view of a sampling tube showing the location of major components including a light absorber made according to the present invention.

In a preferred embodiment of this invention, a short cylindrical body 10 machined to produce at one side thereof a flat face the center of which is encircled by an endless groove having a radially inner wall 11, an opposed, radially outer wall 13a, and a base 15. The wall 11 is inclined at about 30° relative to the axis of the body to form a conical surface. The outer wall 13a also is inclined or undercut, but at a lesser angle, such as 5°, so that it overhangs the base 15. Concentric with the radially inner groove are two radially outer grooves, the intermediate groove being formed by opposed walls 12a, 13 and the outermost groove being formed by opposed walls 12 and 12b. Each of the additional grooves has a base of the same depth as the innermost groove, and the radially inner and outer walls of each groove are parallel to the radially inner and outer walls of the other grooves. The arrangement is such that between each groove is a peak 14 which, due to the undercut construction of the radially outer wall, shades the groove base. Since the face of the body 10 is planar except for the grooves, all of the peaks 14 and the apex of the central cone are coplanar. The radius of each base or valley can be infnitely small, and would otherwise be capable of reflecting a small amount of light axially along said sampling chamber. Equally importantly, incident axial light becomes trapped within the confines of the inclined surfaces and suffers lossy reflection at least five times before emerging, extremely attenuated, in a non-axial direction. This cannot be achieved with the simple cone or inclined plane designs.

In a compromise design for less critical applications in terms of sensitivity, it is possible to utilise two external conical surfaces and not to undercut the internal conical surfaces, resulting in an absorber of lower efficiency but still providing the advantage of short length.

With reference to FIG. 2 the sampling tube includes a light source 60 with associated reflector and a lens 40 near a light sensing device 30. If the area adjacent the light source 60 fills with smoke, light impinges on the particles and is transmitted axially along the tube past light baffles 21 to lens 40 and will impinge upon the light sensor 30. Light baffles 21 and 22 are spaced along the tube to catch stray light impinging at various incident angles. The absorber 10 with its central cone is positioned on the longitudinal axis aligned with the central axis of the lens and the light sensor. Thus, any light which is directed to the back of the sampling chamber will not be reflected back along the sampling chamber toward the sensor 30. Therefore negligable light is reflected axially along the sampling chamber.

The absorber is sealingly mounted in the end of the sampling chamber as a press fit. Sealing of the absorber into the chamber is assured by the provision of O-ring seals 16. This facilitates removal of the absorber to allow access to the sampling chamber for servicing purposes while providing a sealing facility for the chamber where it is required to be operated at other than atmospheric pressure.

I claim:

1. A light absorber comprising a body at one side of which is a face having a center encircled by an annular groove having a base and opposed, radially inner and outer walls, said walls of said groove being so inclined relatively to one another that the radially inner wall forms a conical surface extending from said center inwardly from said face.

2. A light absorber according to claim 1 wherein said annular groove is encircled by at least one additional concentric annular groove, said additional groove having a base and opposed radially inner and outer walls.

3. A light absorber according to claim 2 wherein the radially inner and outer walls of said additional groove parallel the radially inner and outer walls, respectively, of the first mentioned annular groove.

4. A light absorber according to claim 2 wherein the radially outer wall of each of said grooves is undercut and overhangs the base thereof.

5. A light absorber according to claim 1 wherein the radially outer wall of said groove is undercut and overhangs said base.

6. A light absorber according to claim 5 wherein said radially outer wall is undercut by about 5°.

7. A light absorber according to claim 1 wherein said face is planar except for said groove.

8. A light absorber according to claim 1 wherein the radially inner and radially outer walls converge in a direction inwardly of said base.

9. A light absorber according to claim 1 wherein said radially inner wall is inclined at an angle of about 30° inwardly of said face.

10. A light absorber according to claim 1 including a tubular member and means sealingly mounting said body within said tubular member at one end thereof.

11. A light absorber according to claim 1 including a light absorptive coating on said face.

* * * * *

UNITED STATES PATENT AND TRADEMARK OFFICE
CERTIFICATE OF CORRECTION

PATENT NO. : 4,607,915

DATED : August 26, 1986

INVENTOR(S) : Martin T. Cole

It is certified that error appears in the above-identified patent and that said Letters Patent is hereby corrected as shown below:

Column 1, line 16, change "Thuss" to "Thus".

Column 1, line 61, delete "surrounding said"

Column 1, line 62, delete "central cone".

Signed and Sealed this
Ninth Day of December, 1986

*Attest:*

DONALD J. QUIGG

*Attesting Officer*  *Commissioner of Patents and Trademarks*